(12) United States Patent
Wang et al.

(10) Patent No.: US 8,309,727 B2
(45) Date of Patent: Nov. 13, 2012

(54) OPIATE REDUCTION UTILIZING CATALYTIC HYDROGEN TRANSFER REACTION

(75) Inventors: Peter X. Wang, Chesterfield, MO (US); Tao Jiang, St. Louis, MO (US); Gary L. Cantrell, Troy, IL (US); David Wayne Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 470 days.

(21) Appl. No.: 12/595,519

(22) PCT Filed: Apr. 15, 2008

(86) PCT No.: PCT/US2008/004869
§ 371 (c)(1),
(2), (4) Date: Oct. 12, 2009

(87) PCT Pub. No.: WO2008/130553
PCT Pub. Date: Oct. 30, 2008

(65) Prior Publication Data
US 2010/0048905 A1      Feb. 25, 2010

Related U.S. Application Data

(60) Provisional application No. 60/911,950, filed on Apr. 16, 2007.

(51) Int. Cl.
*C07D 489/08* (2006.01)
*C07D 489/02* (2006.01)

(52) U.S. Cl. ............................ 546/45; 546/44

(58) Field of Classification Search ............ 546/45, 546/44
See application file for complete search history.

(56) References Cited

U.S. PATENT DOCUMENTS
2,772,270 A     10/1954     Weiss
(Continued)

FOREIGN PATENT DOCUMENTS
GB          939 287        10/1963
(Continued)

OTHER PUBLICATIONS

Barber et al., "Synthesis of Thebaine and Oripavine from Codeing and Morphine", Journal of Medicinal chemistry, 1975, 18(11), pp. 1074-1077.

(Continued)

*Primary Examiner* — Charanjit Aulakh

(57) ABSTRACT

An improved opiate synthesis scheme is provided. An improvement to the oxidation of oripavine and oripavine derivatives comprises the in-situ formation of the peroxacids required to oxidize the oripavine and oripavine derivatives to form an intermediate. An improvement to the reduction of the intermediate to form oxycodone and oxycodone derivatives comprises reduction utilizing a hydrogen transfer reagent. These improvements allow the production of oxycodone and oxycodone derivatives without isolation of the intermediate, providing a one-pot synthesis method.

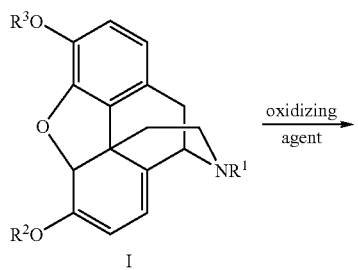

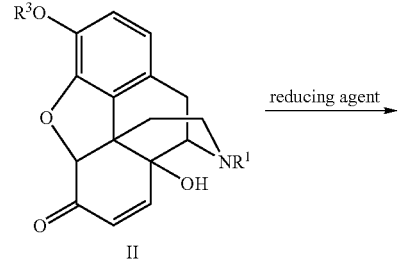

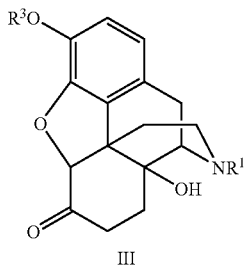

14 Claims, No Drawings

U.S. PATENT DOCUMENTS

| | | | |
|---|---|---|---|
| 3,299,072 A | 10/1963 | Bartels-Keith |
| 3,393,197 A | 10/1967 | Pachter et al. |
| 3,468,891 A | 9/1969 | Bartels-Keith |
| 3,905,981 A | 9/1975 | Olofson et al. |
| 4,277,604 A | 7/1981 | Dauben et al. |
| 4,472,253 A | 9/1984 | Schwartz |
| 4,639,520 A | 1/1987 | Kavka |
| 4,795,813 A | 1/1989 | Schwartz |
| 5,071,985 A | 12/1991 | Andre et al. |
| 5,112,975 A | 5/1992 | Wallace |
| 5,668,285 A | 9/1997 | Rice et al. |
| 5,869,669 A | 2/1999 | Huang et al. |
| 5,922,876 A | 7/1999 | Huang et al. |
| 5,948,788 A | 9/1999 | Huang et al. |
| 6,008,354 A | 12/1999 | Huang et al. |
| 6,008,355 A | 12/1999 | Huang et al. |
| 6,177,567 B1 | 1/2001 | Chiu et al. |
| 6,262,266 B1 | 7/2001 | Chiu et al. |
| 6,365,742 B1 | 4/2002 | Mudryk et al. |
| 6,376,221 B1 | 4/2002 | Fist et al. |
| 6,864,370 B1 | 3/2005 | Lin et al. |
| 7,071,336 B2 | 7/2006 | Francis et al. |
| 2002/0106761 A1 | 8/2002 | Fist et al. |
| 2002/0143183 A1 | 10/2002 | Chiu et al. |
| 2004/0017891 A1 | 1/2004 | Endo |
| 2004/0077863 A1 | 4/2004 | Scammells et al. |
| 2005/0038250 A1 | 2/2005 | Linders et al. |
| 2005/0038251 A1 | 2/2005 | Francis et al. |
| 2005/0222188 A1 | 10/2005 | Chapman et al. |
| 2006/0173029 A1 | 8/2006 | Chapman et al. |
| 2008/0132702 A1 | 6/2008 | Kupper |

FOREIGN PATENT DOCUMENTS

| | | |
|---|---|---|
| WO | WO 2005/028483 | 3/2005 |
| WO | WO 2005/097801 | 10/2005 |
| WO | WO 2006/094672 | 9/2006 |
| WO | WO 2008/048711 | 4/2008 |

OTHER PUBLICATIONS

Coop et al., "L-Selectride as a General Reagent for the O-Demethylation and N-Decarbomethoxylation of Opium Alkaloids and Derivatives", J. Org. Chem., 1998, 63, pp. 4392-4396, XP 002485052.

Coop et al., "Direct and Simple O-Demethylation of Thebaine to Oripavine", J. Org. chem.., 1996, 61, p. 6774.

Krassnig et al., "Optimization of the synthesis of oxycodone and 5-methyloxycodone", Archiv der Pharmazia, 1996, 329(6), pp. 325-326.

Ninan et al., "An improved synthesis of noroxymorphone", Tetrahedron, 48(32), 1992, pp. 6709-6716.

Schmidhammer et al., "Synthesis, structure elucidation, and pharmacological evaluation of 5- methyl-oxymorphone . . . ", Helvetica Chimica Acta, 1988, 71(7), pp. 1801-1804.

OPIATE REDUCTION UTILIZING CATALYTIC HYDROGEN TRANSFER REACTION

CROSS REFERENCE TO RELATED APPLICATIONS

This application is a national stage application of PCT/US2008/004869, filed Apr. 15, 2008, which claims the benefit of U.S. Provisional Application No. 60/911,950 filed Apr. 16, 2007.

BACKGROUND OF INVENTION

Oxymorphone and its derivatives are conventionally produced by O-demethylation of oxycodone with conventional O-demethylation reagents such as BBr$_3$ and HBr. The yield for these reactions varies, typically from 30% to as high as 80%. Unfortunately, oxycodone is an expensive starting material.

Alternatively, oxymorphone can be produced by oxidation of oripavine, followed by reduction of the intermediate, as illustrated in Scheme 1:

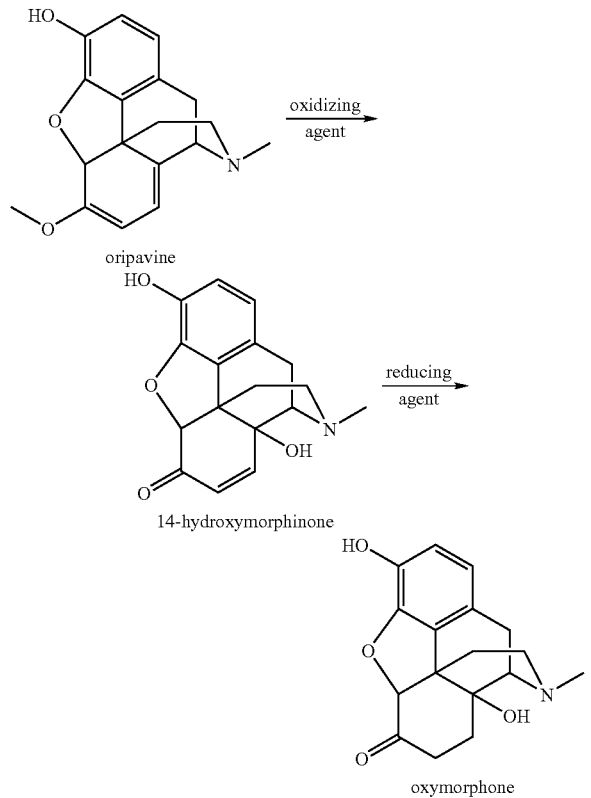

The Scheme 1 method is analogous to the method of making oxycodone from thebaine, which is widely practiced in the industry. The conventional synthesis of oxycodone from thebaine comprises oxidizing thebaine to form 14-hydroxycodeinone followed by catalytic hydrogenation of 14-hydroxycodeinone to form oxycodone. The conventional oxidant is an acid in combination with hydrogen peroxide or another common oxidant.

The use of oripavine is desirable because of its competitive pricing and structural similarity to oxymorphone, compared to thebaine. Unfortunately, the use of oripavine is challenging because oripavine has multiple reactive sites by virtue of attached functional groups. The Scheme 1 reaction yields significant by-products that cannot be easily isolated or removed, resulting in lowered reaction yields. These low yields from oripavine to oxymorphone render this synthetic route impractical on a commercial scale. There is no known reference in the literature to a practical synthesis utilizing oripavine as the starting material for the formation of oxymorphone.

The conventional oxidation processes utilized in opiate synthesis reactions, for example the oxidation of thebaine, typically utilize a peroxyacid, or more specifically peroxyacetic acid, since it is well suited and effective for this reaction. Unfortunately, the use of peroxyacids is dangerous, requiring expensive and time consuming safeguards for preparing, transporting and handling high concentrations of peroxyacetic acid under industrial conditions.

The reduction of 14-hydroxy-6-keto-opiate compounds formed by the oxidation of thebaine or oripavine is typically carried out by catalytic hydrogenation. Although the catalytic hydrogenation for the reduction of an α,β-unsaturated ketone to the corresponding saturated ketone is well known and commonly practiced, expensive pressure reactors are required to contain the potentially explosive hydrogen atmosphere. Therefore, there is a need to provide a simpler, safer synthetic route.

SUMMARY OF INVENTION

In one illustrative aspect of the present invention, a method for converting a compound according to Formula I or a pharmaceutically acceptable salt thereof to a compound according to Formula II or a pharmaceutically acceptable salt thereof is provided. The method comprises substantially dissolving a compound according to Formula I in a solvent to form a reaction mixture; forming at least one peroxyacid in the reaction mixture; and allowing the at least one peroxyacid to oxidize the compound according to Formula I to from the compound according to Formula II.

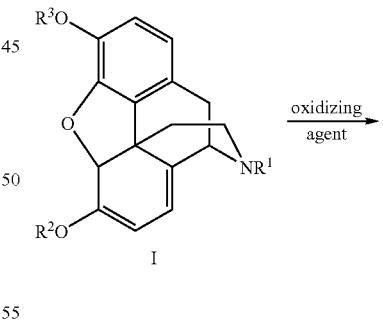

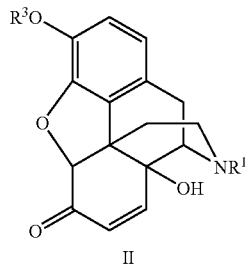

wherein $R^1$, $R^2$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group.

In another aspect of the present invention, there is provided a method for converting a compound according to Formula II or a pharmaceutically acceptable salt thereof into a compound according to Formula III or a pharmaceutically acceptable salt thereof. The method comprises reducing the compound according to Formula II with a hydrogen transfer reagent to form the compound according to Formula III

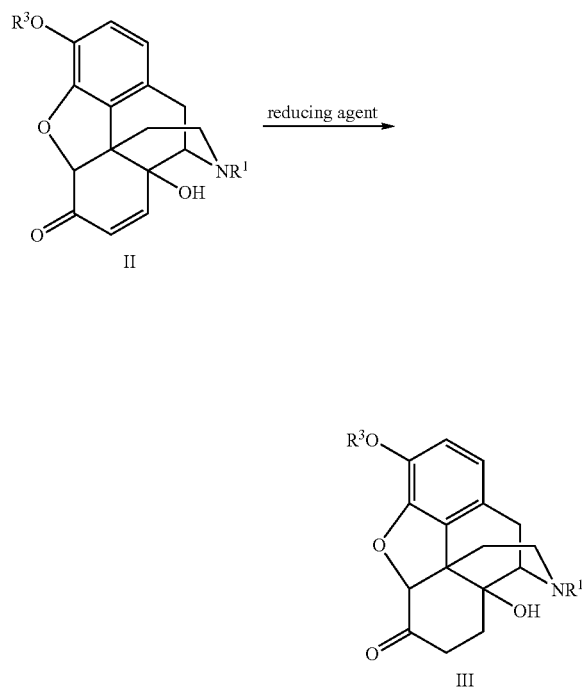

wherein $R^1$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group.

In yet another aspect of the present invention, there is provided a method for preparing an opiate compound according to Formula III or a pharmaceutically acceptable salt thereof. The method comprises substantially dissolving a compound according to Formula I or a pharmaceutically acceptable salt thereof in at least one solvent to form a reaction mixture; adding at least one oxidant and at least one acid to the reaction mixture, wherein the at least one oxidant and the at least one acid react to form at least one peroxyacid; allowing the peroxyacid to oxidize the compound according to Formula I to form a compound according to Formula II or a pharmaceutically acceptable salt thereof; reducing the compound according to Formula II opiate with at least one hydrogen transfer reagent to form a compound according to Formula III or a pharmaceutically acceptable salt thereof

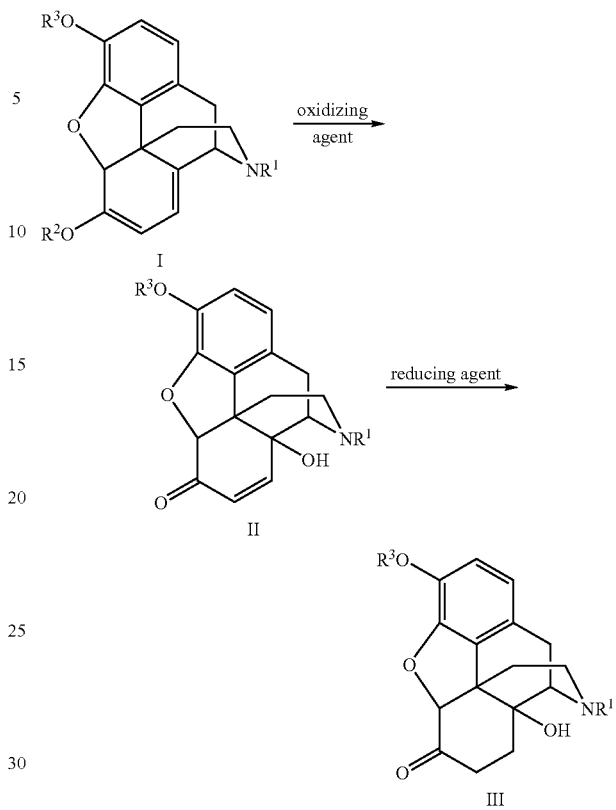

wherein $R^1$, $R^2$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group.

DETAILED DESCRIPTION

The conventional reaction Scheme 1 applies more generally to derivatives of oripavine as illustrated in Scheme 2. Derivatives according to Formula I or a pharmaceutically acceptable salt thereof, hereinafter Formula I compound(s), may be oxidized to form derivatives according to Formula II or a pharmaceutically acceptable salt thereof, hereinafter Formula II compound(s), which are then reduced to derivatives according to Formula III or a pharmaceutically acceptable salt thereof, hereinafter Formula III compound(s).

Scheme 2

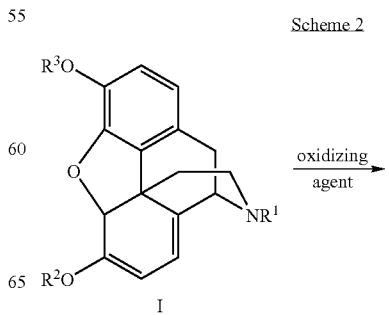

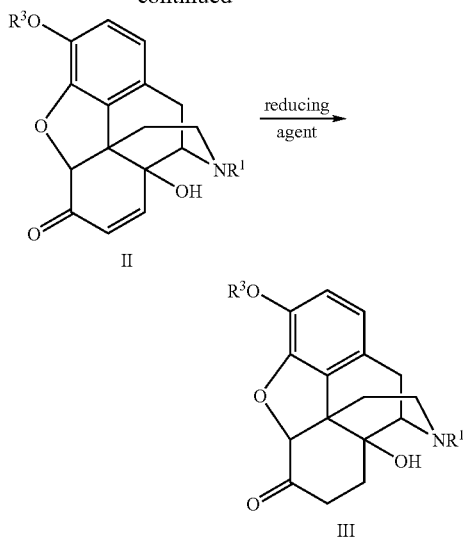

wherein $R^1$, $R^2$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group. Suitable aryl groups include phenyl and substituted phenyl.

There is provided an improved synthetic route for the conversion of the Formula I compound to the Formula III compound. The improved synthetic route described herein includes one improvement to the oxidizing step, the conversion of the Formula I compound into the Formula II compound, and another improvement to the reducing step, the conversion of the Formula II compound into the Formula III compound. These improvements may be implemented together or separately, as desired.

The oxidation step improvement comprises the in-situ formation of at least one peroxyacid. Conventional oxidation of the Formula I compound to form the Formula II compound involves a peroxyacid; for example, peroxyacetic acid. Peroxyacetic acid is generally prepared by the reaction of hydrogen peroxide with glacial acetic acid in the presence of sulfuric acid. Peroxyacetic acid, and peroxyacids in general, are unstable, dangerous, and expensive to store and transport. It has been unexpectedly determined that peroxyacids can be successfully generated in-situ, in the presence of a compound of the Formula I compound formula, without the expected oxidation of the intermediate ketone or phenoxyl functional groups (wherein $R^3$=H).

In an illustrative example, peroxyacetic acid or peroxyformic acid are formed in presence of a compound with the general formula of Formula I compound. Once the peroxyacetic acid or peroxyformic acid is generated it is continuously consumed by reaction with Formula I compound to form Formula II compound. Therefore, the peroxyacid never reaches concentrations high enough to lead to dangerous conditions. In addition to the safety improvements, there are no transportation or storage issues attendant to in-situ formation of peroxyacids.

The in-situ formation is achieved through the reaction of an acid according to the formula $R^4CO_2H$ (wherein $R^4$ is H or an alkyl of 1-20 carbons) and an oxidant. Suitable peroxyacids include $HCO_3H$, $CH_3CO_3H$, m-$ClC_6H_4CO_3H$, $C_6H_4CO_3H$, $R^4CO_3H$ wherein $R^4$ is selected from H and an alkyl of 1-20 Carbons, and mixtures thereof. Suitable oxidants are well known in the art and include hydrogen peroxide, $K_2O_2$, $Na_2O_2$, $Li_2O_2$, $Cs_2O_2$, $K_2SO_5$, $Na_2SO_5$ and mixtures thereof.

The temperature of the in-situ peroxyacid formation reaction is not critical, but is typically maintained between $-5°$ C. and $80°$ C., but may be at any temperature warm enough so that the solvent does not freeze. Higher temperatures may be utilized, but typically result in increased impurity formation.

The rate of the oxidation reaction may be accelerated by the addition of a strong acid. The strong acid catalyzes the reaction of the oxyacid with hydrogen peroxide to form the peroxyacid. In the absence of an additional strong acid, the reaction will proceed, but will typically be very slow, as is known in the art. Peroxyacid is typically formed by the reaction of oxyacid with hydrogen peroxide in the presence of the strong acid. Suitable rate accelerating acids include $H_2SO_4$, $H_3PO_4$, $MeSO_3H$, HCl, p-toluenesulfonic acid and mixtures thereof. Most strong acids are suitable to function as a strong acid catalyst, as is well known in the art.

The second improvement of the present invention relates to the reduction step converting Formula II compound to Formula III compound. In conventional opiate synthesis, the reduction reaction is a catalytic hydrogenation reaction. In catalytic hydrogenation, a hydrogen molecule, $H_2$, reacts with the double bond of the Formula II compound in the presence of a catalyst, such as Pd on carbon. This reaction requires a high pressure hydrogen atmosphere; therefore, requiring a high pressure reactor for the reaction.

In the present invention, it has been unexpectedly discovered that a catalytic hydrogen transfer reduction reaction can satisfactorily and selectively hydrogenate the Formula II compound double bond. In an illustrative example, $HCO_2H$ reacts with Formula II compound to reduce the double bond and form a saturated ketone. The hydrogen transfer reduction reaction takes place in the presence of metal catalyst. Suitable metal catalysts are well known in the art and include transition metal on carbon, such as Pd/C, Pt/C, Ru/C, Rh/C, late transition metal oxides, such as $PdO_2$, $PtO_2$ and complexes of these metals with phosphine ligands, and mixtures thereof.

The hydrogen transfer reaction has several advantages over the conventional catalytic hydrogenation reaction. During the hydrogen transfer reduction reaction, $HCO_2H$ decomposes into 2H for double bond reduction and one $CO_2$ molecule as side product. Since $HCO_2H$ is a liquid at room temperature, the reaction does not require the use of a high pressure reactor for the reaction. Therefore the improved method is economical, as it can reduce investment on expensive high pressure reactors. In addition, the reaction can unexpectedly take place in the presence of oxygen. Typically, the presence of oxygen leads to side products including over-oxidation of the ketone or phenoxyl functional groups, but in the present improvement the reaction unexpectedly proceeds as desired.

Suitable hydrogen transfer reagents include $HCO_2H$, $HCO_2H/HCO_2NH_4$, $HCO_2H/HCO_2Na$, $HCO_2H/NEt_3$, HCHO, HCHO/$NR^5_3$ wherein $R^5$ groups are independently selected from H, alkyl, aryl and mixtures thereof, all of which are common hydrogen transfer reagents well known in the art.

The temperature of the hydrogen transfer reaction is not considered critical, although the temperature is typically maintained between about −5° C. and about 110° C. Increased yields of the Formula III compound have been observed at temperatures of about 60° C. to about 110° C.

Advantageously, the present invention may be utilized as a "one-pot" synthesis, without isolation of the intermediate Formula II compound, if desired, as both the improved oxidation and improved reduction may be performed in the same solvent. Conventional reactions require isolation of the intermediate, both to remove impurities and to allow for a change of solvents.

Specifically, the improved oxidation and improved reduction of the present invention may be carried out in aqueous medium, or in a mixture of water and organic solvents. Any solvent that substantially dissolves in about 5 to about 95% water may be utilized. Suitable organic solvents include $R^6OH$ ($R^6$ is an alkyl group of 1-8 carbons), THF, ethyl acetate, ether and mixtures thereof.

In a non-limiting embodiment of the present invention, a strong acid may be added to increase the rate of conversion of oxyacid to peroxyacid and therefore speed up the oxidation of the Formula I compound to the Formula II compound. Once the oxidation is completed, a base is added to neutralize the acid and raise the pH to a level suitable for reduction. It has been determined that a pH of about 2 to about 4 will result in less over reduction than a pH of less than 1. Suitable bases include NaOH, KOH, $Na_2CO_3$, $K_2CO_3$, $NaHCO_3$, $KHCO_3$, $HCO_2Na$, $CH_3CO_2Na$, $NEt_3$ and mixtures thereof.

In an illustrative, non-limiting example of the present invention utilizing the two reaction improvements disclosed herein are utilized in a one-pot synthesis. The Formula I compound is dissolved in $HCO_2H/H_2O$. $H_2O_2$ is added as an oxidant and $H_2SO_4$ is added as a catalyst. In the presence of a strong acid such as $H_2SO_4$, $H_2O_2$ reacts with the $HCO_2H$ to form peroxyacetic acid, $HCO_3H$. The in-situ formed $HCO_3H$ reacts with the Formula I compound to form the intermediate Formula II compound and $HCO_2H$. Upon addition of Pd/C as catalyst, the catalyst and $HCO_2H$ initiate the hydrogen transfer reduction to convert the Formula II compound into the Formula III compound.

In an alternative embodiment of the reduction step, upon completion of the oxidation of the Formula I compound to the Formula II compound, $NEt_3$ is added to neutralize the excess $H_2SO_4$ and a portion of the $HCO_2H$, resulting in a mixture of $HCO_2H$ and $HCO_2H/NEt_3$. These reagents are suitable hydrogen transfer reagents. Upon addition of the catalyst Pd/C, the hydrogen transfer reduction is initiated and Formula II compound is converted to Formula III compound.

In another alternative embodiment, upon completion of the oxidation of the Formula I compound to the Formula II compound, $HCO_2Na$ is added to neutralize any excess $H_2SO_4$, resulting in a formation of $HCO_2H$. This reagent is a suitable hydrogen transfer reagent. Upon addition of a catalyst such as Pd/C, the hydrogen transfer reduction is initiated and Formula II compound is converted to Formula III compound.

In yet another illustrative, non-limiting example, the peroxyacid is formed in-situ according to the improved oxidation step described herein, while the reduction step is accomplished through the conventional reductive method.

In still another illustrative, non-limiting example, the oxidation step is accomplished through the conventional oxidative method, in combination with the improved reductive step described herein.

EXAMPLES

Example 1

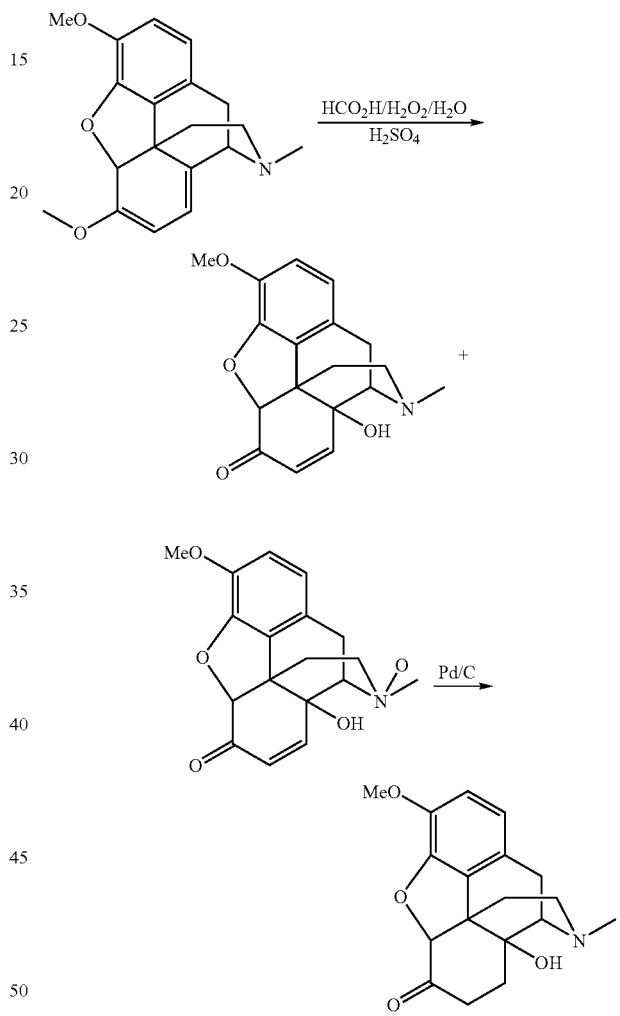

Dried thebaine (3.2 g, 95% wt/wt %) was dissolved in $HCO_2H/H_2O$ (6 mL/9 mL) to form a reaction solution. $H_2O_2$ (50% wt/wt, 0.9 mL) and $H_2SO_4$ (0.30 g) were added to the reaction solution, which was stirred at 20° C. until HPLC data showed that the thebaine was completely converted to 14-hydroxycodeinone, about 3 to 6 hours. 0.3 g of 5% Pd/C was then added and the resulting mixture was heated at 45° C. for 2 hours, and then at 60° C. for an additional 2 hours, after which HPLC showed greater than 95% conversion from 14-hydroxycodeinone. The reaction mixture was filtered at 60° C. and the resulting filtrate was cooled to room temperature. c-$NH_4OH$ was added slowly until the pH of the mixture was raised sufficiently to yield a precipitate. The resulting mixture was stirred at room temperature for 1 hour and filtered. The recovered solid was washed with water (3×15 mL), and dried under house vacuum at 75° C. for 18 hour to give 1.8 g of product.

Example 2

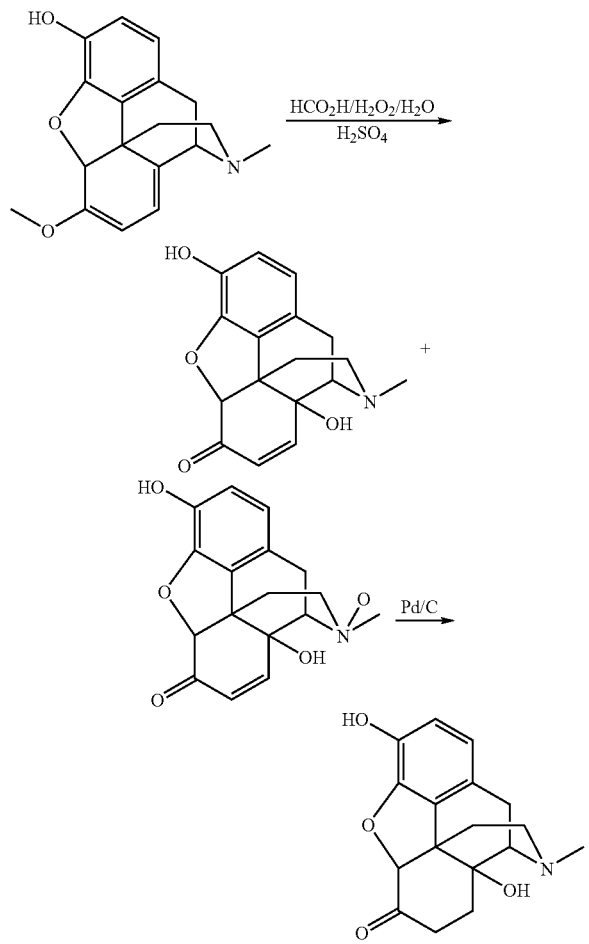

Dried oripavine (3.0 g, 95% wt/wt %) was dissolved in $HCO_2H/H_2O$ (6.0 mL/9.0 mLg) to form a reaction solution. $H_2O_2$ (50% wt/wt, 0.70 mL) and $H_2SO_4$ (0.45 mL) were added to the reaction solution, which was stirred at 20° C. until HPLC data showed that the oripavine was completely converted to 14-hydroxycodeinone, about 20-30 hours. 0.3 g of 5% Pd/C was then added and the resulting mixture was stirred for 30 minutes at room temperature. $HCO_2Na$ (0.6 g) and $NEt_3$ (7.5 mL) were added. The mixture was heated at 45° C. for 2 hours, and then at 80° C. for an additional 4-8 hours, after which HPLC showed complete disappearance of 14-hydroxymorphinone. The reaction mixture was cooled to 60° C. and filtered. The resulting filtrate was cooled to room temperature. $c-NH_4OH$ was added slowly until the pH of the mixture was adjusted to 9.2-10.0 to yield a precipitate. The resulting mixture was stirred at room temperature for 1 hour and filtered. The recovered solid was washed with water (3×15 mL), and dried under house vacuum at 75° C. for 18 hour to give 1.6 g of product.

Example 3

Dried oripavine (3.0 g, 95% wt/wt %) was dissolved in $HCO_2H/H_2O$ (6.0 mL/9.0 mLg) to form a reaction solution. $H_2O_2$ (50% wt/wt, 0.70 mL) and $H_2SO_4$ (0.45 mL) were added to the reaction solution, which was stirred at 20° C. until HPLC data showed that the oripavine was completely converted to 14-hydroxycodeinone, about 20-30 hours. 0.3 g of 5% Pd/C was then added and the resulting mixture was stirred for 30 minutes at room temperature. $NEt_3$ (8.8 mL) was added. The mixture was heated at 45° C. for 2 hours, and then at 80° C. for an additional 4-8 hours, after which HPLC showed that complete disappearance of 14-hydroxymorphinone. The reaction mixture was cooled to 60° C. and filtered. The resulting filtrate was cooled to room temperature. $c-NH_4OH$ was added slowly until the pH of the mixture was adjusted to 9.2-10.0 to yield a precipitate. The resulting mixture was stirred at room temperature for 1 hour and filtered. The recovered solid was washed with water (3×15 mL), and dried under house vacuum at 75° C. for 18 hour to give 1.8 g of product.

There has been described a novel process for the preparation of opiate compounds. While the method of this invention has been described with reference to specific compounds and examples, no intention is made by such reference to limit the scope of this invention unless expressly stated. Various modifications may be made in the materials and sequence of process steps as well as process combinations, which are adapted to suit the various process steps without departing from this invention, limited only by the appended claims. The foregoing description is given for clarity of understanding only and no unnecessary limitations should be understood there from, as modifications will be obvious to those skilled in the art.

Specifically, it is noted that the reactions and compounds of the present invention are equally applicable to the use of pharmaceutically acceptable salts of the compounds, as is well known in the art. The compound salts may be utilized as starting materials, or may be formed during the reaction process, for example the formation of sulfate and bisulfate compounds when sulfuric acid is present in the reaction mixture. The use and formation of these salts in well known in the pharmaceutical industry.

The invention claimed is:

1. A method for converting a compound according to Formula II or a pharmaceutically acceptable salt thereof into a compound according to Formula III or a pharmaceutically acceptable salt thereof, the method comprising:

reducing the compound according to Formula II or a pharmaceutically acceptable salt thereof with a hydrogen transfer reagent in the presence of a metal catalyst to form the compound according to Formula III or a pharmaceutically acceptable salt thereof

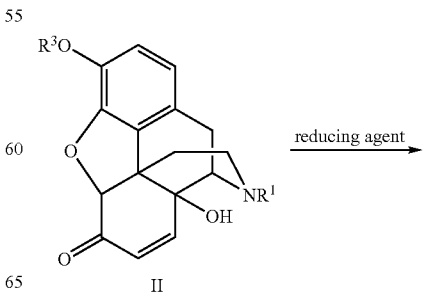

II

-continued

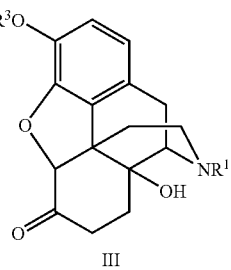

wherein $R^1$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group, and wherein:
(a) the hydrogen transfer reagent is selected from the group consisting of $HCO_2H/HCO_2NH_4$, $HCO_2H/HCO_2Na$, $HCO_2H/NEt_3$, HCHO and $HCHO/NR_3$, wherein each R group is independently selected from H, alkyl, aryl and mixtures thereof; or
(b) the reaction temperature is maintained at about 60° C. to about 110° C.

2. The method of claim 1 further comprising reducing the compound of Formula II or a pharmaceutically acceptable salt thereof in the presence of oxygen to form a compound according to Formula III or a pharmaceutically acceptable salt thereof.

3. The method of claim 1 further comprising reducing the compound of Formula II or a pharmaceutically acceptable salt thereof under substantially atmospheric pressure to form a compound according to Formula III or a pharmaceutically acceptable salt thereof.

4. The method of claim 1 wherein the hydrogen transfer reagent is selected from the group consisting of $HCO_2H/HCO_2NH_4$, $HCO_2H/HCO_2Na$, $HCO_2H/NEt_3$, HCHO and $HCHO/NR_3$, wherein each R group is independently selected from H, alkyl, aryl and mixtures thereof and wherein the reaction temperature is maintained at about 60° C. to about 110° C.

5. The method of claim 1 wherein the metal catalyst is selected from the group consisting of transition metals on carbon, late transition metal oxides, phosphine ligand metal complexes, and mixtures thereof.

6. The method of claim 1 wherein the hydrogen transfer reagent is selected from the group consisting of $HCO_2H/HCO_2NR_4$, $HCO_2H/HCO_2Na$, $HCO_2H/NEt_3$, HCHO and $HCO_2H/HCO_2NH_4$, $HCO_2H/HCO_2Na$, $HCO_2H/NEt_3$, HCHO and $HCHO/NR_3$, wherein each R group is independently selected from H, alkyl, aryl and mixtures thereof and the temperature is substantially maintained at about −5° C. to about 110° C.

7. A method for preparing an opiate compound according to Formula III or a pharmaceutically acceptable salt thereof, the method comprising:
substantially dissolving a compound according to Formula I or a pharmaceutically acceptable salt thereof in at least one solvent to form a reaction mixture;
adding at least one oxidant and at least one acid to the reaction mixture, wherein the at least one oxidant and the at least one acid react to form at least one peroxyacid;
allowing the peroxyacid to oxidize the compound according to Formula I or a pharmaceutically acceptable salt thereof to form a compound according to Formula II or a pharmaceutically acceptable salt thereof;
reducing the compound according to Formula II or a pharmaceutically acceptable salt thereof with at least one hydrogen transfer reagent in the presence of a metal catalyst to form a compound according to Formula III or a pharmaceutically acceptable salt thereof

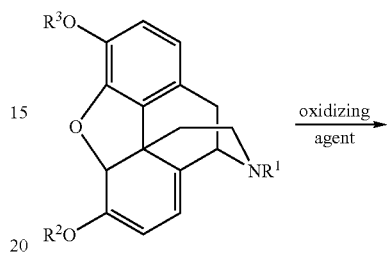

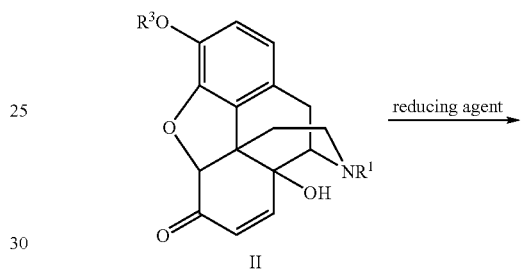

wherein $R^1$, $R^2$ and $R^3$ are independently selected from H; benzyl; 1-8 carbon alkane sulfonyl; p-tosyl; an alkyl group of 1-20 carbons; a substituted alkyl group, wherein the alkyl group is substituted with phenyl, substituted phenyl, 1-8 carbon alkoxyl or phenoxyl groups; and RCO, wherein R is an alkyl group of 1-20 carbons or an aryl group, and wherein:
(a) the hydrogen transfer reagent is selected from the group consisting of $HCO_2H/HCO_2NH_4$, $HCO_2H/HCO_2Na$, $HCO_2H/NEt_3$, HCHO and $HCHO/NR_3$, wherein each R group is independently selected from H, alkyl, aryl and mixtures thereof; or
(b) Formula II or a pharmaceutically acceptable salt thereof is reduced at a temperature of from about 60° C. to about 110° C.

8. The method of claim 7 further including maintaining the reaction mixture at a temperature high enough to prevent oxidation of ketone or phenoxyl functional groups.

9. The method of claim 7 wherein Formula II or a pharmaceutically acceptable salt thereof is reduced at a temperature of from 60° C. to 110° C.

10. The method of claim 7 wherein the peroxyacid is formed in the reaction mixture by reacting an oxidant with an acid.

11. The method of claim 7 further including adding at least one strong acid selected from the group consisting of $H_2SO_4$, $H_3PO_4$, $MeSO_3H$, HCl, p-toluenesulfonic acid and mixtures thereof.

12. The method of claim 7 further comprising reducing the compound of Formula II or a pharmaceutically acceptable salt thereof in the presence of oxygen to form a compound according to Formula III or a pharmaceutically acceptable salt thereof.

13. The method of claim 7 wherein the hydrogen transfer reagent is selected from the group consisting of $HCO_2H/HCO_2NH_4$, $HCO_2H/HCO_2Na$, $HCO_2H/NEt_3$, HCHO and $HCHO/NR_3$, wherein each R group is independently selected from H, alkyl, aryl and mixtures thereof and wherein Formula II or a pharmaceutically acceptable salt thereof is reduced at a temperature of from about 60° C. to about 110° C.

14. The method of claim 7 wherein the metal catalyst is selected from the group consisting of transition metals on carbon, late transition metal oxides, phosphine ligand metal complexes, and mixtures thereof.

* * * * *